United States Patent
Haetzelt et al.

(10) Patent No.: US 11,104,688 B2
(45) Date of Patent: Aug. 31, 2021

(54) PRO-FRAGRANCES AND METHOD OF PREPARATION THEREOF

(71) Applicant: Henkel AG & Co. KGaA, Duesseldorf (DE)

(72) Inventors: Andre Haetzelt, Eimeldingen (DE); Andreas Bauer, Kaarst (DE); Marc Weyhe, Krefeld (DE); Andreas Gerigk, Erkelenz (DE); Michael Dischmann, Krefeld (DE); Sascha Wilhelm Schaefer, Mettmann (DE)

(73) Assignee: HENKEL AG & CO. KGAA, Dusseldorf (DE)

( * ) Notice: Subject to any disclaimer, the term of this patent is extended or adjusted under 35 U.S.C. 154(b) by 0 days.

(21) Appl. No.: 16/646,170

(22) PCT Filed: Sep. 25, 2018

(86) PCT No.: PCT/EP2018/075923
§ 371 (c)(1),
(2) Date: Mar. 11, 2020

(87) PCT Pub. No.: WO2019/068511
PCT Pub. Date: Apr. 11, 2019

(65) Prior Publication Data
US 2020/0270270 A1 Aug. 27, 2020

(30) Foreign Application Priority Data

Oct. 4, 2017 (DE) ..................... 10 2017 122 983.3

(51) Int. Cl.
*A61K 8/18* (2006.01)
*A61Q 13/00* (2006.01)
*A61K 8/00* (2006.01)
*C07D 498/04* (2006.01)
*C07D 263/06* (2006.01)
*C11B 9/00* (2006.01)

(52) U.S. Cl.
CPC .......... *C07D 498/04* (2013.01); *C07D 263/06* (2013.01); *C11B 9/0003* (2013.01); *C11B 9/0061* (2013.01); *C11B 9/0096* (2013.01)

(58) Field of Classification Search
CPC ... C07D 263/06; C07D 498/04; C11B 9/0003; C11B 9/0096; C11B 9/0061
USPC .................................................. 512/10, 8, 1
See application file for complete search history.

(56) References Cited

U.S. PATENT DOCUMENTS

| | | |
|---|---|---|
| 2008/0305063 A1 | 12/2008 | Huchel et al. |
| 2009/0312231 A1 | 12/2009 | Huchel et al. |
| 2012/0004328 A1* | 1/2012 | Huchel ................... C11D 3/50 514/788 |
| 2013/0288940 A1 | 10/2013 | Huchel et al. |
| 2020/0247817 A1* | 8/2020 | Haetzelt ................. A61Q 13/00 |

FOREIGN PATENT DOCUMENTS

| | | |
|---|---|---|
| DE | 102009001570 A1 | 9/2010 |
| EP | 2144917 B1 | 9/2012 |
| WO | 2007087977 A1 | 8/2007 |
| WO | 2012084292 A1 | 6/2012 |
| WO | 2016074697 A1 | 5/2016 |
| WO | 2016074699 A1 | 5/2016 |

OTHER PUBLICATIONS

International search report from parallel PCT Patent Application PCT/EP2018/075923 dated Nov. 2, 2018, 8 pages (for reference purposes only).

* cited by examiner

*Primary Examiner* — Jessica Whiteley
(74) *Attorney, Agent, or Firm* — Viering Jentschura & Partner

(57) ABSTRACT

A compound based on 1-Aza-3,7-dioxabicyclo[3.3.0]octane (bicyclic oxazolidine derivative) substituted with 3-(4-isobutyl-2-methylphenyl)propyl represented by formula (I)

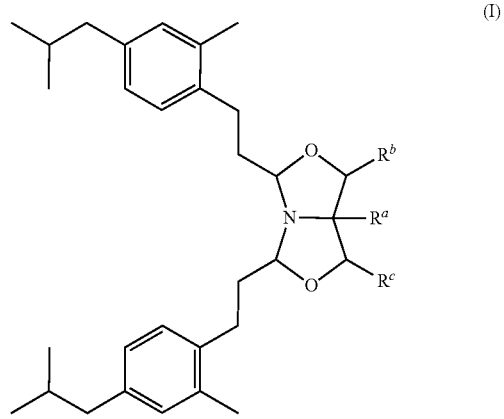

is disclosed.

15 Claims, No Drawings

PRO-FRAGRANCES AND METHOD OF PREPARATION THEREOF

CROSS-REFERENCE TO RELATED APPLICATIONS

The present application is a national stage entry according to 35 U.S.C. § 371 of PCT application No.: PCT/EP2018/075923 filed on Sep. 25, 2018; which claims priority to German Patent Application Serial No.: 10 2017 122 983.3, which was filed on Oct. 4, 2017; which is incorporated herein by reference in its entirety and for all purposes.

TECHNICAL FIELD

Compounds based on 1-Aza-3,7-dioxabicyclo[3.3.0]octane (bicyclic oxazolidine derivative) may be substituted with 3-(4-isobutyl-2-methylphenyl)propyl, and more particularly may be used in pro-fragrance compositions.

BACKGROUND

In addition to the use of fragrances in detergent, cleaning, fabric softening and cosmetic composition, it is also known to use pro-fragrances in such compositions. By analogy with pro-drugs, pro-fragrances are chemical derivatives of a fragrance, which for example reduce the volatility of the fragrance and allow a delayed release of the fragrance over time under ambient conditions. By derivatization of fragrances, such as aldehyde or ketone fragrances, the vapor pressure of these compounds can be lowered. Since the derivatization reaction is reversible, the chemically bound aldehyde or ketone fragrance may, under certain conditions, e.g., ambient conditions, be released, which may lead to a prolonged scent impression.

The base compound used for forming the pro-fragrance is a 1-aza-3,7-dioxabicyclo[3.3.0]octane (bicyclic oxazolidine derivative). Such oil-soluble substituted monocyclic and bicyclic oxazolidines are disclosed for the use as additives in automatic transmission fluids, for example, in U.S. Pat. No. 4,277,353. Examples described therein include reaction products of optionally substituted 2-amino-1,3-propanediols with paraformaldehyde and isobutyraldehyde.

Pro-fragrance compounds based on 1-aza-3,7-dioxabicyclo[3.3.0]octane derivatives are for example disclosed in WO 2007/087977 A1. In this reference a generic formula for those compounds is disclosed together with a long list of exemplary compounds for aldehydes or ketones that are commonly used as fragrances.

An object of the present invention was to identify further oxazolidine compounds of the general formula of WO 2007/087977 A1, that provide for a prolonged scent perception, in particular in comparison to the explicitly disclosed examples of this reference.

SUMMARY

The present inventors have surprisingly found that 1-aza-3,7-dioxabicyclo[3.3.0]octane (bicyclic oxazolidine derivatives) compounds substituted with 3-(4-isobutyl-2-methylphenyl)propyl, produced by reacting the corresponding aldehyde 3-(4-isobutyl-2-methylphenyl)propanal (commercially available under the tradename nympheal) with serinol or a derivative thereof, provide for improved scent longlastingness and intensity compared to other known 1-aza-3,7-dioxabicyclo[3.3.0]octane compounds, for example those substituted with 3-(4-tert-butylphenyl)-2-methylpropyl (using the corresponding aldehyde 3-(4-tert-butylphenyl)-2-methylpropanal (lilial)).

In a first aspect, a compound based on 1-aza-3,7-dioxabicyclo[3.3.0]octane may be substituted with 3-(4-isobutyl-2-methylphenyl)propyl represented by formula (I)

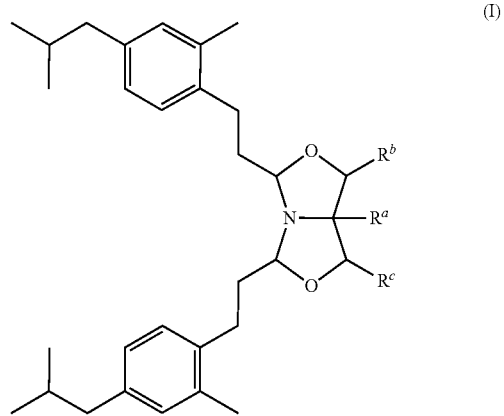

wherein $R^a$ is hydrogen or a $C_{1-20}$ alkyl group which can optionally be substituted with hydroxyl groups and/or amine groups and/or in which up to 8 —$CH_2$— groups which are not adjacent to each other can be substituted by —O—, such as $R^a$ is hydrogen or $C_{1-6}$ alkyl, alternatively $R^a$ is hydrogen or methyl, or $R^a$ is hydrogen;

$R^b$ and $R^c$ are independently selected from hydrogen or $C_{1-6}$ alkyl, such as $R^b$ and $R^c$ are independently selected from hydrogen and methyl, alternatively $R^b$ and $R^c$ are both hydrogen.

In a second aspect, a mixture of at least one compound of formula (I) as described above may be mixed with at least one compound of formula (II)

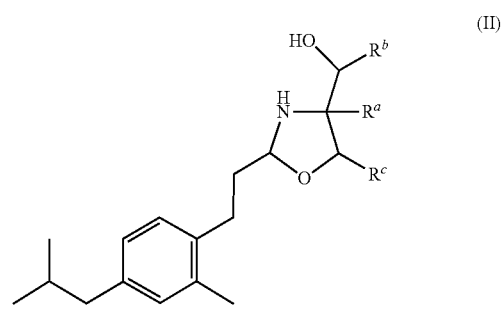

wherein $R^a$ is hydrogen or a $C_{1-20}$ alkyl group which can optionally be substituted with hydroxyl groups and/or amine groups and/or in which up to 8 —$CH_2$— groups which are not adjacent to each other can be substituted by —O—, such as $R^a$ is hydrogen or $C_{1-6}$ alkyl, alternatively $R^a$ is hydrogen or methyl, or $R^a$ is hydrogen;

$R^b$ and $R^c$ are independently selected from hydrogen or $C_{1-6}$ alkyl, such as $R^b$ and $R^c$ are independently selected from hydrogen and methyl, alternatively $R^b$ and $R^c$ are both hydrogen.

DETAILED DESCRIPTION

The inventive compounds of formulae (I) and (II) are useful as pro-fragrances, as the bound aldehyde is released over time and provides for the desired scent experience.

"One or more", as used herein, relates to at least one and comprises 1, 2, 3, 4, 5, 6, 7, 8, 9 or more of the referenced species. Similarly, "at least one" means one or more, i.e. 1, 2, 3, 4, 5, 6, 7, 8, 9 or more. "At least one", as used herein in relation to any component, refers to the number of chemically different molecules, i.e. to the number of different types of the referenced species, but not to the total number of molecules. For example, "at least one aldehyde" means that at least one type of molecule falling within the definition for an aldehyde is used but that also two or more different molecule types falling within this definition can be present, but does not mean that only one molecule of said aldehyde is present.

If reference is made herein to a molecular weight, this reference refers to the weight average molecular weight $M_w$, if not explicitly stated otherwise. The weight average molecular weight can be determined by gel permeation chromatography.

All percentages given herein in relation to the compositions or formulations relate to weight % relative to the total weight of the respective composition or formula, if not explicitly stated otherwise.

It has been surprisingly found by the inventors that compounds based on 1-aza-3,7-dioxabicyclo[3.3.0]octane substituted with 3-(4-isobutyl-2-methylphenyl)propyl have an improved prolonged scent impression compared to the compounds of this type known in the prior art. Furthermore, it has been found that the deposition of such bicyclic compounds on solid surfaces such as textiles, skin or hard surfaces is improved.

The compounds of formulae (I) and (II) can be obtained by a method that comprises reacting at least one compound of formula (III)

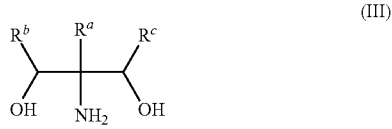

(III)

wherein $R^a$ is hydrogen or a $C_{1-20}$ alkyl group which can optionally be substituted with hydroxyl groups and/or amine groups and/or in which up to 8 —$CH_2$— groups which are not adjacent to each other can be substituted by —O—, such as $R^a$ is hydrogen or $C_{1-6}$ alkyl, alternatively $R^a$ is hydrogen or methyl, or $R^a$ is hydrogen;

$R^b$ and $R^c$ are independently selected from hydrogen or $C_{1-6}$ alkyl, such as $R^b$ and $R^c$ are independently selected from hydrogen and methyl, alternatively $R^b$ and $R^c$ are both hydrogen; with
a compound of formula

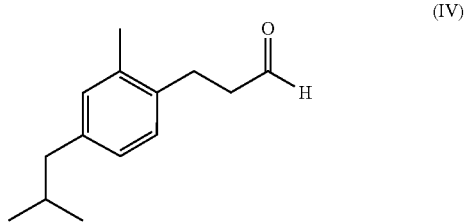

(IV)

in a ring forming reaction. In this reaction the aldehyde group of 3-(4-isobutyl-2-methylphenyl)propanal reacts with the hydroxyl and the amino groups of the compound of formula (III) to form the compounds of formula (I) and/or (II).

The compounds of general formula (III) are derived from 2-amino-1,3-propanediol (serinol). By producing the bicyclic compounds, it is possible to achieve a high degree of loading of the 2-amino-1,3-propanediols, so that the use of smaller amounts of 2-amino-1,3-propanediols is possible. This achieves a prolongation of the scent impression even with smaller amounts of 2-amino-1,3-propanediols, which can lead to cost advantages and also avoids the introduction of large quantities of chemicals into detergent, cleaning, fabric softening or cosmetic compositions.

As can be seen from the above, it is also possible to use monocyclic compounds based on 2-amino-1,3-propanediols, i.e. the compounds of formula (II). These are generated as byproducts in the synthesis of the compounds of formula (I). It is possible to achieve a high degree of loading of the 2-amino-1,3-propanediols, so that bicyclic oxazolidines are generally used.

In compounds according to formula (I) $R^a$ is hydrogen or a $C_{1-20}$ alkyl group which can optionally be substituted with hydroxyl groups and/or amine groups and/or in which up to 8 —$CH_2$— groups which are not adjacent to each other can be substituted by —O—, such as $R^a$ is hydrogen or $C_{1-6}$ alkyl, alternatively $R^a$ is hydrogen or methyl, or $R^a$ is hydrogen;

$R^b$ and $R^c$ are independently selected from hydrogen or $C_{1-6}$ alkyl, such as $R^b$ and $R^c$ are independently selected from hydrogen and methyl, alternatively $R^b$ and $R^c$ are both hydrogen.

In various embodiments, $R^a$ is hydrogen or methyl and $R^b$ and $R^c$ are hydrogen. Non-limiting embodiments may include $R^a$ is methyl and $R^b$ and $R^c$ are hydrogen. Alternatively, $R^a$ to $R^c$ are all hydrogen. This provides for an improved long-lastingness of the scent and high intensity even after prolonged periods of time.

To produce the compounds of formula (I) the amino alcohol of formula (III) is reacted with an aldehyde of formula (IV) which is 3-(4-isobutyl-2-methylphenyl)propanal, commercially available under the name nympheal and having the CAS No. 1637294-12-2. According to one embodiment, the compounds of general formula (I) are derived from a 2-amino-1,3-propanediol molecule of formula (III) and two aldehyde molecules of formula (IV). In the reaction of less than stoichiometric amounts of aldehydes, monocyclic compounds are also present in the product mixture. The amount of bicyclic compounds to monocyclic compounds may be adjusted easily through the choice of the molar ratios between aldehyde and 2-amino-1,3-propanediol. Large amounts of bicyclic structures are especially useful. Such mixtures contain at least 50 wt.-%, such as at least 65 wt.-%, or at least 80 wt.-% of bicyclic structures, based on the total weight of the compounds. In various embodiments, this means that in the mixtures of compounds according to formulae (I) and (II), the amount of compounds of formula (I) is higher than 50 mol.-% relative to the total amount of compounds of formulae (I) and (II), such as higher than 70 mol.-%, alternatively higher than 80 mol.-%, or at least 90 mol.-%.

The reaction is performed in a suitable solvent or in situ, such as in a suitable solvent. Suitable solvents include, for example, hydrocarbons containing aromatics, in particular toluene. The reaction is carried out at a temperature in the range of 80 to 150° C., such as 100 to 140° C., alternatively at 120° C. For example, as the starting material the compound of general formula (III) is used together with the aldehyde and the solvent under nitrogen atmosphere. This reaction mixture is then heated, such as from 5 minutes to 20 hours, alternatively from 1 to 10 hours, or from 6 to 8 hours, whereupon the solids gradually go into solution. The reaction is finished when no more water as by-product of the reaction is produced. The mixture is heated under reflux on a water separator. The resulting reaction product is isolated by conventional methods, for example by drying in vacuum, and purified if necessary.

The compounds are used as pro-fragrances. The term "pro-fragrance" describes in general derivatives of aldehyde and ketone fragrances, which release the original aldehydes and ketones under ambient conditions. Ambient conditions are typical ambient conditions in the human biosphere and/or the conditions encountered on human skin. The compounds of general formula (I) and (II) disintegrate slowly under ambient conditions in a reversal of the synthesis process, releasing the original aldehydes. Accordingly, the compounds may be used as pro-fragrances.

The at least one compound may be used as the only fragrance substance, but it is also possible to use mixtures of fragrances, which are comprised only partially of the at least one compound. In particular, fragrance mixtures containing 1 to 50 wt.-%, such as 5 to 40.-wt.-%, and in particular max. 30 wt.-% of the at least one compound of formula (I) or the mixture of compounds of formulae (I) and (II), based on the total weight of the fragrance mixture may be used. In a non-limiting embodiment, the at least one compound or compound mixture can be used together with further fragrance compounds different from the compounds of formulae (I) and (II). By the use of additional perfume compounds in the compositions, e.g., detergent or cleaning compositions, it is possible to create a variety of characteristics of the final product, which are only possible by using them in combination with the at least one compound or the mixture of the compounds. For example, it is possible to divide the total perfume content (fragrance content) of a composition, for example a detergent or cleaning composition, into two portions, x and y, wherein portion x comprises the compounds and portion y comprises traditional scent substances, like perfume oils.

The fragrance substances (or perfume compounds, with these two terms being used interchangeably herein) that may be additionally incorporated are not subject to any restrictions. Individual perfume substance compounds of natural or synthetic origin, e.g., of the type of esters, ethers, aldehydes, ketones, alcohols and hydrocarbons may thus be used as the perfume substance including perfume oils. Fragrance compounds of the ester type include, for example, benzyl acetate, phenoxyethyl isobutyrate, p-tert-butylcyclohexyl acetate, linalyl acetate, dimethylbenzylcarbinyl acetate (DMBCA), phenylethyl acetate, benzyl acetate, ethylmethyl phenyl glycinate, allylcyclohexyl propionate, styrallyl propionate, benzyl salicylate, cyclohexylsalicylate, floramat, melusat and jasmacyclate. The ethers include, for example, benzylethyl ether and ambroxan; the aldehydes include, for example, the linear alkanals with 8 to 18 carbon atoms, citral, citronellal, citronellyl oxyacetaldehyde, cyclamenaldehyde, lilial and bourgeonal; the ketones include, for example, the ionones, α-isomethylionone and methyl cedryl ketone; the alcohols include anethole, citronellol, eugenol, geraniol, linalool, phenylethyl alcohol and terpineol; the hydrocarbons include mainly terpenes such as limonene and pinene. However, mixtures of various fragrance substances which jointly produce an attractive scent note may be used.

Such fragrance substances may also contain mixtures of natural perfume substances such as those accessible from plant sources, e.g., pine oil, citrus oil, jasmine oil, patchouli oil, rose oil or ylang-ylang oil. Also suitable are muscatel sage oil, chamomile oil, clove oil, lemon balm oil, mint oil, cinnamon leaf oil, linden blossom oil, juniper berry oil, vetiver oil, olibanum oil, galbanum oil and labdanum oil as well as orange blossom oil, neroli oil, orange peel oil and sandalwood oil.

Other traditional fragrance substances that may be used within the scope include, for example, the essential oils such as angelica root oil, anise oil, arnica blossom oil, sweet basil oil, bay oil, champaca blossom oil, silver fir oil, fir cone oil, elemi oil, eucalyptus oil, fennel oil, spruce needle oil, galbanum oil, geranium oil, ginger grass oil, guaiac wood oil, gurjun balsam oil, helichrysum oil, ho oil, ginger oil, iris oil, cajeput oil, calamus oil, chamomile oil, camphor oil, canaga oil, cardamom oil, cassia oil, pine needle oil, copaiba balsam oil, coriander oil, spearmint oil, caraway oil, cumin oil, lavender oil, lemon grass oil, lime oil, mandarin oil, lemon balm oil, ambrette seed oil, myrrh oil, clove oil, neroli oil, niaouli oil, olibanum oil, origanum oil, palmarosa oil, patchouli oil, Peru balsam oil, petitgrain oil, pepper oil, peppermint oil, allspice oil, pine oil, rose oil, rosemary oil, sandalwood oil, celery seed oil, spike lavender oil, star anise oil, turpentine oil, thuja oil, thyme oil, verbena oil, vetiver oil, juniper berry oil, vermouth oil, wintergreen oil, ylang-ylang oil, ysop oil, cinnamon oil, cinnamon leaf oil, citronella oil, lemon oil and cypress oil as well as compounds selected from the group of ambrettolide, ambroxan, α-amylcinnamaldehyde, anethole, anise aldehyde, anise alcohol, anisole, anthranilic acid methyl ester, acetophenone, benzylacetone, benzaldehyde, benzoic acid ethyl ester, benzophenone, benzyl alcohol, benzyl acetate, benzyl benzoate, benzyl formate, benzyl valerate, borneol, bornyl acetate, boisambrene forte, α-bromostyrene, n-decylaldehyde, n-dodecylaldehyde, eugenol, eugenol methyl ether, eucalyptol, farnesol, fenchone, fenchyl acetate, geranyl acetate, geranyl formate, heliotropin, heptin carboxylic acid methyl ester, heptaldehyde, hydroquinone dimethyl ester, hydroxycinnamyl aldehyde, hydroxycinnamyl alcohol, indole, iron, isoeugenol, isoeugenol methyl ether, isosafrol, jasmine, camphor, carvacrol, carbon, p-cresol methyl ether, coumarin, p-methoxyacetophenone, methyl-n-amyl ketone, methyl anthranilic acid methyl ester, p-methylacetophenone, methyl chavicol, p-methylquinoline, methyl β-naphthyl ketone, methyl n-nonylaldehyde, nonyl alcohol, n-octylaldehyde, p-oxyacetphenone, pentadecanolide, β-phenylethyl alcohol, phenylacetaldehyde-dimethylacetal, phenylacetic acid, pulegon, safrole, salicylic acid isoamyl ester, salicylic acid methyl ester, salicylic acid hexyl ester, salicylic acid cyclohexyl ester, santalol, sandelice, skatol, terpineol, thyme, thymol, troenan, γ-undelactone, vanillin, veratrum aldehyde, cinnamyl aldehyde, cinnamyl alcohol, cinnamic acid, cinnamic acid ethyl ester, cinnamic acid benzyl ester, diphenyl oxide, limonene, linalool, linayl acetate and linalyl propionate, melusat, menthol, menthone, methyl-n-heptenone, pinene, phenyl acetaldehyde, terpinyl acetate, citral, citronellal and mixtures thereof.

All fragrance substances disclosed herein, can be used in the compositions or agents in free or encapsulated form or both. Specifically, the compounds of formulae (I) and (II) can be used in free or encapsulated form or both. As they are used as precursors, they are used in free, i.e. non-encapsulated form. In various embodiments, they can be combined with encapsulated fragrances, wherein these may also include free nympheal. As capsules, microcapsules can be used, all of which are known in the art and include, without limitation, aminoplast and acrylate microcapsules. The microcapsules in which the fragrances or pro-fragrances are encapsulated may have a core-shell morphology, with the shell being typically formed of a polymer, or alternatively may have the form of matrix particles in which the fragrance substances are entrapped.

The at least one compound of formula (I) or the mixture of compounds of formulae (I) and (II) can be used in perfume compositions, can be present in those in amounts of 0.001 to 100 wt.-% relative to the total weight of the perfume composition, such as in amounts of 0.1 to 90 wt.-%, such as 1 to 90 wt.-%, 2 to 85 wt.-%, 5 to 75 wt.-% or 10 to 50 wt.-%.

EXAMPLES

Synthesis of 1-aza-3,7-dioxabicyclo[3.3.0]octanes

AA1: General Operating Procedure for Synthesis of 1-aza-3,7-dioxabicyclo[3.3.0]octanes, Amino Alcohol/Aldehyde Ratio 1:2

The amino alcohol and the aldehyde were combined in a 1:2 molar ratio in toluene as the solvent under nitrogen atmosphere. The reaction mixture was heated to 120° C., whereupon the amino alcohol slowly goes into solution. The mixture was refluxed using a water separator for 7 hours. The resulting product was obtained by removing the solvent by rotating vacuum distillation and drying in high vacuum.

AA2: General Operating Procedure for Synthesis of 1-aza-3,7-dioxabicyclo[3.3.0]octanes, Amino Alcohol/Aldehyde Ratio 1:2 In Situ The amino alcohol was combined with the aldehyde in a 1:2 molar ratio under nitrogen atmosphere. The reaction mixture was heated to 100-140° C., whereupon the reactants go into solution slowly or melt. The reaction mixture is heated until no more reaction water can be distilled off. The transparent slightly yellowish solution was dried in a high vacuum.

Example 1: Synthesis of 2,8-bis[2-[2-methyl-4-(2-methylpropyl)phenyl]ethyl]-3.7-dioxa-1-azabicyclo[3.3.0]octane According to the general procedure AA2 22.75 g 2-amino-1,3-propandiol (CAS 534-03-2) and 103.02 g 3-(4-isobutyltolyl)propionaldehyde (Nympheal) (CAS 1637294-12-2) were heated to 120° C. during 5 hours to afford 115.65 g (100%) of the desired compound as a yellow oil.

$R_f$ (1% v/v $Et_3N$ in $Et_2O$/nHex 1:1)=0.52. GC (45° C.—0 min; 300° C.—14 min; 15° C./min): 20.2 min, 21.1 min. $^1H$ NMR (400 MHz, $CDCl_3$) –δ (ppm) 7.10-7.00 (m, 2H), 6.95-6.85 (m, 4H), 4.50 (t, J=5.5 Hz, 2H), 4.12 (dd, J=8.5 Hz, 6.5 Hz, 2H), 3.87 (m, 1H), 3.68 (dd, J=8.5 Hz, 4.7 Hz, 2H), 2.75-2.62 (m, 4H), 2.40 (m, 4H), 2.29 (s, 6H), 1.91-1.72 (m, 6H), 0.98-0.72 (m, 12H) $^{13}C$ NMR (101 MHz, $CDCl_3$) –δ (ppm) 139.3 (s, 2C), 137.0 (s, 2C), 136.6 (s, 2C), 131.1 (d, 2C), 128.4 (d, 2C), 126.7 (d, 2C), 96.7 (d, 1C), 69.7 (t, 2C), 62.3 (d, 2C), 45.0 (t, 2C), 35.8 (t, 2C), 30.2 (d, 2C), 28.2 (t, 2C), 22.4 (q, 4C), 19.3 (q, 2C). MS (ESI+): 464 $[M+H]^+$ (100%).

Comparative Example 1

Instead of 3-(4-isobutyltolyl)propionaldehyde the aldehyde lilial was used. The synthesis was carried out as described for the inventive example above.

Olfactory Test

The aldehydes nympheal and lilial in free form as well as the compound of Example 1 and Comparative Example 1 were tested for their performance as follows. The aforementioned compounds were mixed into a standard solid powder detergent (65 g dose (Persil)) so that the initial scent intensity of the free compounds nympheal and lilial on the one hand and the scent intensity of the respective oxazolidine precursors was about the same. The scent intensity was evaluated by four trained perfumers on a scale of 0 to 5, where 5 is the highest score and 0 stands for no perception of scent. The scent was evaluated on textiles after washing 3.5 kg laundry in a standard washing machine (standard program at 40° C.). Three different types of laundry were used, namely blended fabric, cotton and polyester. The scent was evaluated on the laundry being in wet state directly after washing, in dry state immediately after the laundry had dried and 7 days after the washing/drying. The assessment was performed 5 times, respectively and the results are displayed as average values. The results are displayed in Table 1 below.

Definition of the Scale 5 very strong 4 strong 3 pleasant 2 perceptible 1 not perceptible

TABLE 1

Results of the olfactory test.

| Compound | Wet (1) | Wet (2) | Wet (3) | Dry (1) | Dry (2) | Dry (3) | After 7 days (1) | After 7 days (2) | After 7 days (3) |
|---|---|---|---|---|---|---|---|---|---|
| Example 1 | 3.80 | 3.70 | 4.38 | 3.60 | 3.70 | 3.80 | 3.33 | 4.33 | 3.83 |
| Nympheal | 2.40 | 2.10 | 2.50 | 2.30 | 2.30 | 2.30 | 2.5 | 3.00 | 3.00 |
| Comparative Example 1 | 2.13 | 2.38 | 2.38 | 2.00 | 2.50 | 2.50 | 2.75 | 3.25 | 3.00 |
| Lilial | 2.13 | 2.50 | 2.25 | 2.00 | 2.75 | 2.25 | 2.75 | 3.00 | 3.00 |

(1) = blended fabric, (2) = cotton, (3) = polyester

Scent impression of the dosing units before washing Nympheal = 3.3; Example 1 = 2.38; Lilial = 3.4; Comparative Example 1 = 2.2.

As can be seen by the results shown in Table 1, the compounds of example 1 show an improved long-lasting scent impression compared to the compounds of comparative example 1.

The invention claimed is:

1. A pro-fragrance composition comprising a compound based on 1-Aza-3,7-dioxabicyclo[3.3.0]octane substituted with 3-(4-isobutyl-2-methylphenyl)propyl represented by formula (I):

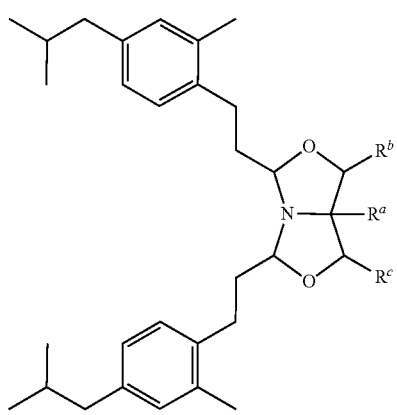

wherein:

$R^a$ is hydrogen, a $C_{1-20}$ alkyl, or combinations thereof;

the $C_{1-20}$ alkyl is optionally substituted with hydroxyl groups, amine groups, or combinations thereof, up to 8 —CH$_2$— groups of the $C_{1-20}$ alkyl are substituted by —O— groups; and the up to 8 —CH$_2$— groups are not adjacent to each other; and $R^b$ and $R^c$ are independently selected from hydrogen, $C_{1-6}$ alkyl, or combinations thereof; and at least one compound of formula (II):

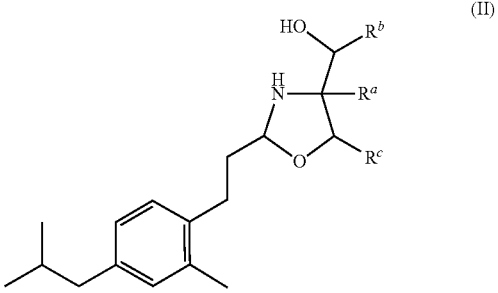

wherein:

$R^a$ is hydrogen, a $C_{1-20}$ alkyl, or combinations thereof;

the $C_{1-20}$ alkyl is optionally substituted with hydroxyl groups, amine groups, or combinations thereof; up to 8 —CH$_2$— groups of the $C_{1-20}$ alkyl are substituted by —O— groups; and the up to 8 —CH$_2$— groups are not adjacent to each other; and $R^b$ and $R^c$ are independently selected from hydrogen, $C_{1-6}$ alkyl, or combinations thereof.

2. A method for preparing a compound according to claim 1 by reacting at least one compound of formula (III)

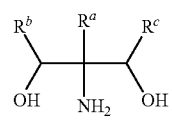

wherein:

$R^a$ is hydrogen, a $C_{1-20}$ alkyl, or combinations thereof;

the $C_{1-20}$ alkyl is optionally substituted with hydroxyl groups, amine groups, or combinations thereof, up to 8 —CH$_2$— groups of the $C_{1-20}$ alkyl are substituted by —O— groups; and the up to 8 —CH$_2$— groups are not adjacent to each other; and $R^b$ and $R^c$ are independently selected from hydrogen, $C_{1-6}$ alkyl, or combinations thereof;

with a compound of formula (IV)

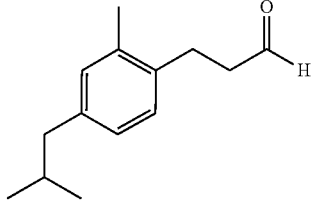

(IV)

in a ring forming reaction.

3. The pro-fragrance composition of claim 1, wherein the compound of formula (I) releases the fragrance compound of formula (IV):

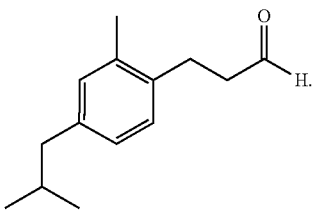

(IV)

4. The pro-fragrance composition of claim 1, further comprising one or more additional fragrance compounds different from that of the compound of formula (I) and from that of the compound of formula (II).

5. The pro-fragrance composition of claim 1, wherein $R^a$ of the compound of formula (I) is a $C_{1-6}$ alkyl.

6. The pro-fragrance composition of claim 1, wherein $R^a$ of the compound of formula (I) is methyl.

7. The pro-fragrance composition of claim 1, wherein $R^a$ of the compound of formula (I) is hydrogen.

8. The pro-fragrance composition of claim 1, wherein $R^b$ and $R^c$ of the compound of formula (I) are independently selected from hydrogen, methyl, or combinations thereof.

9. The pro-fragrance composition of claim 1, wherein $R^b$ and $R^c$ of the compound of formula (I) are both hydrogen.

10. The pro-fragrance composition of claim 1, wherein $R^a$ of the compound of formula (II) is a $C_{1-6}$ alkyl.

11. The pro-fragrance composition of claim 1, wherein $R^a$ of the compound of formula (II) is methyl.

12. The pro-fragrance composition of claim 1, wherein $R^a$ of the compound of formula (II) is hydrogen.

13. The pro-fragrance composition of claim 1, wherein $R^b$ and $R^c$ of the compound of formula (II) are independently selected from hydrogen, methyl, or combinations thereof.

14. The pro-fragrance composition of claim 1, wherein $R^b$ and $R^c$ of the compound of formula (II) are both hydrogen.

15. A method for preparing a compound based on 1-Aza-3,7-dioxabicyclo[3.3.0]octane substituted with 3-(4-isobutyl-2-methylphenyl)propyl represented by formula (I):

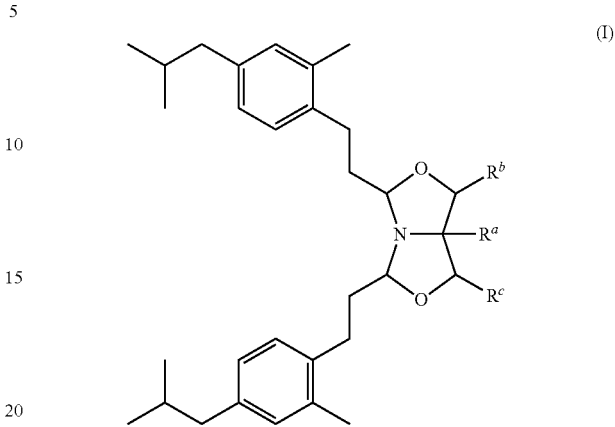

(I)

wherein:
$R^a$ is hydrogen, a $C_{1-20}$ alkyl, or combinations thereof;
the $C_{1-20}$ alkyl is optionally substituted with hydroxyl groups, amine groups, or combinations thereof, up to 8 —$CH_2$— groups of the $C_{1-20}$ alkyl are substituted by —O— groups; and the up to 8 —$CH_2$— groups are not adjacent to each other; and
$R^b$ and $R^c$ are independently selected from hydrogen, $C_{1-6}$ alkyl, or combinations thereof;

wherein the method comprises:
reacting at least one compound of formula (III)

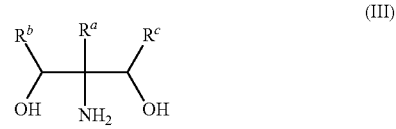

(III)

wherein:
$R^a$ is hydrogen, a $C_{1-20}$ alkyl, or combinations thereof;
the $C_{1-20}$ alkyl is optionally substituted with hydroxyl groups, amine groups, or combinations thereof, up to 8 —$CH_2$— groups of the $C_{1-20}$ alkyl are substituted by —O— groups; and the up to 8 —$CH_2$— groups are not adjacent to each other; and
$R^b$ and $R^c$ are independently selected from hydrogen, $C_{1-6}$ alkyl, or combinations thereof;
with a compound of formula (IV)

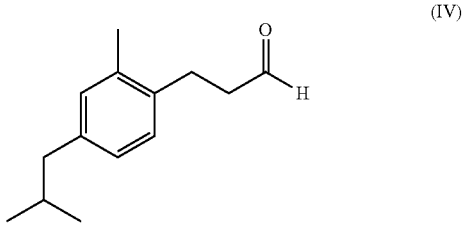

(IV)

in a ring forming reaction.

* * * * *